United States Patent
Wasserman (10) Patent No.: US 12,397,151 B2
(45) Date of Patent: Aug. 26, 2025

(54) ARRAYS FOR DELIVERING TUMOR TREATING FIELDS (TTFIELDS) WITH SETS OF ELECTRODE ELEMENTS HAVING INDIVIDUALLY ADJUSTABLE ACTIVE AREAS

(71) Applicant: Novocure GmbH, Root (CH)

(72) Inventor: Yoram Wasserman, Haifa (IL)

(73) Assignee: Novocure GmbH, Baar (CH)

(*) Notice: Subject to any disclaimer, the term of this patent is extended or adjusted under 35 U.S.C. 154(b) by 774 days.

(21) Appl. No.: 17/670,731

(22) Filed: Feb. 14, 2022

(65) Prior Publication Data
US 2022/0257927 A1 Aug. 18, 2022

Related U.S. Application Data

(60) Provisional application No. 63/150,425, filed on Feb. 17, 2021.

(51) Int. Cl.
*A61N 1/00* (2006.01)
*A61N 1/04* (2006.01)
*A61N 1/36* (2006.01)

(52) U.S. Cl.
CPC ....... *A61N 1/0476* (2013.01); *A61N 1/36002* (2017.08); *A61N 1/36031* (2017.08)

(58) Field of Classification Search
None
See application file for complete search history.

(56) References Cited

U.S. PATENT DOCUMENTS

| | | |
|---|---|---|
| 5,233,987 A | 8/1993 | Fabian et al. |
| 6,868,289 B2 | 3/2005 | Palti |
| 7,016,725 B2 | 3/2006 | Palti |
| 7,089,054 B2 | 8/2006 | Palti |
| 7,136,699 B2 | 11/2006 | Palti |

(Continued)

FOREIGN PATENT DOCUMENTS

| | | |
|---|---|---|
| CN | 106794354 A | 5/2017 |
| WO | 2021137094 A1 | 7/2021 |

OTHER PUBLICATIONS

International Search Report and Written Opinion issued in application No. PCT/IB2022/051295 dated May 16, 2022.

*Primary Examiner* — John R Downey
(74) *Attorney, Agent, or Firm* — Potomac Law Group, PLLC (57) ABSTRACT

Tumor treating fields (TTFields) can be delivered to a subject's body using electrode elements that are arranged in sets, wherein each set includes a respective first electrode element and a respective second electrode element disposed in thermal contact with each other. Individual first conductors provide an electrically conductive path between each of the first electrode elements and a respective pin of a connector. And a second conductor provides an electrically conductive path between all of the second electrode elements and another pin of the connector. Temperature sensors are disposed in thermal contact with each set of electrode elements. Because the electrode elements are arranged in sets, the current that flows through any given set can be reduced (with respect to its maximum value) by switching off the first electrode element within the given set, in order to prevent the area that corresponds to the given set from overheating.

8 Claims, 8 Drawing Sheets

(56) References Cited

U.S. PATENT DOCUMENTS

| | | |
|---|---|---|
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 11,191,956 B2 | 12/2021 | Giladi et al. |
| 2006/0167499 A1 | 7/2006 | Palti |
| 2007/0225766 A1 | 9/2007 | Palti |
| 2007/0239213 A1 | 10/2007 | Palti |
| 2009/0076366 A1 | 3/2009 | Palti |
| 2009/0182394 A1 | 7/2009 | Bachinski |
| 2012/0283726 A1 | 11/2012 | Palti |
| 2014/0330268 A1 | 11/2014 | Palti et al. |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1* | 2/2018 | Wasserman .......... A61N 1/3603 |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0117963 A1 | 4/2019 | Travers et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0114141 A1 | 4/2020 | Bomzon et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0269041 A1 | 8/2020 | Zeevi et al. |
| 2020/0368525 A1 | 11/2020 | Maag et al. |
| 2021/0031031 A1 | 2/2021 | Wasserman et al. |
| 2021/0038584 A1 | 2/2021 | Voloshin-Sela |
| 2021/0060334 A1 | 3/2021 | Avraham et al. |
| 2021/0069503 A1 | 3/2021 | Tran et al. |
| 2021/0187277 A1 | 6/2021 | Wasserman et al. |
| 2021/0196348 A1 | 7/2021 | Wasserman |
| 2021/0199640 A1 | 7/2021 | Patel et al. |
| 2021/0203250 A1 | 7/2021 | Wasserman |
| 2021/0268247 A1 | 9/2021 | Story et al. |
| 2021/0299440 A1 | 9/2021 | Deslauriers et al. |
| 2021/0308446 A1 | 10/2021 | Alon et al. |
| 2021/0330950 A1 | 10/2021 | Hagemann et al. |
| 2021/0346694 A1 | 11/2021 | Wasserman et al. |
| 2021/0379362 A1 | 12/2021 | Smith et al. |
| 2021/0408383 A1 | 12/2021 | Kalra et al. |
| 2022/0095997 A1 | 3/2022 | Wasserman |
| 2022/0096821 A1 | 3/2022 | Kirson et al. |
| 2022/0118249 A1 | 4/2022 | Bomzon et al. |

\* cited by examiner

PRIOR ART

ARRAYS FOR DELIVERING TUMOR TREATING FIELDS (TTFIELDS) WITH SETS OF ELECTRODE ELEMENTS HAVING INDIVIDUALLY ADJUSTABLE ACTIVE AREAS

CROSS REFERENCE TO RELATED APPLICATIONS

This Application claims the benefit of U.S. Provisional Application 63/150,425, filed Feb. 17, 2021, which is incorporated herein by reference in its entirety.

BACKGROUND

Figure 1:
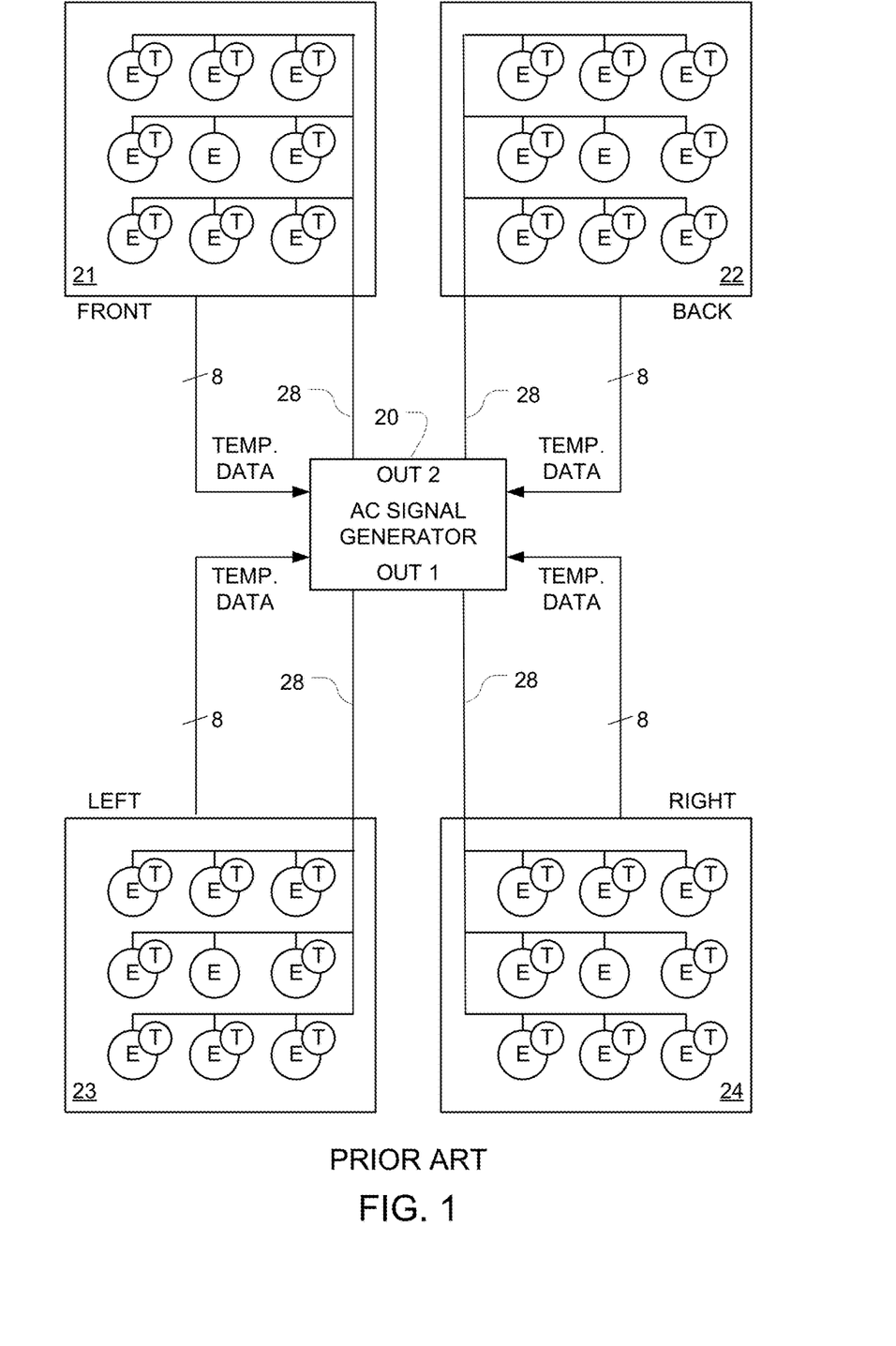
FIG. 1 is a schematic representation of the prior art Optune® system for delivering TTFields.
Figure 2A:
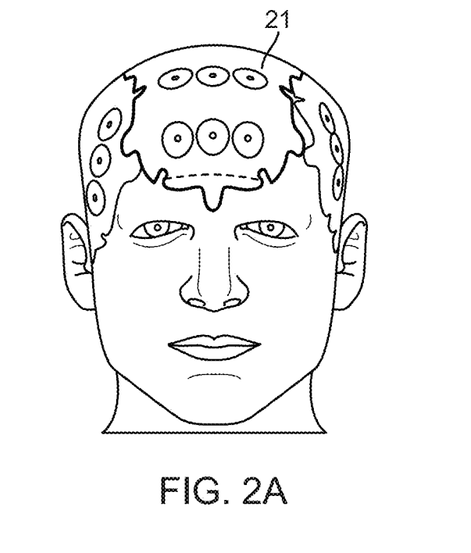
FIGS. 2A-2D depict the positioning of transducer arrays on a person's head for treating a brain tumor.
Figure 2B:
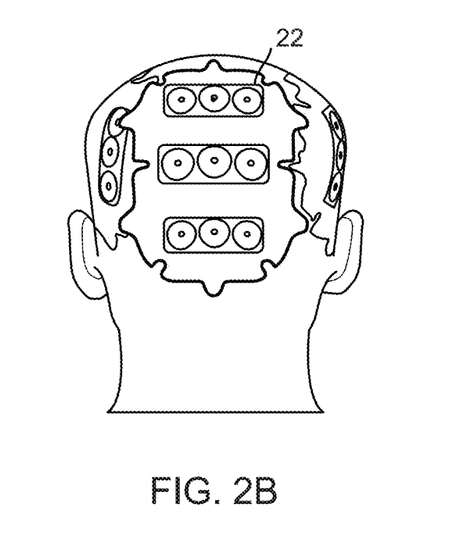
Figure 2C:
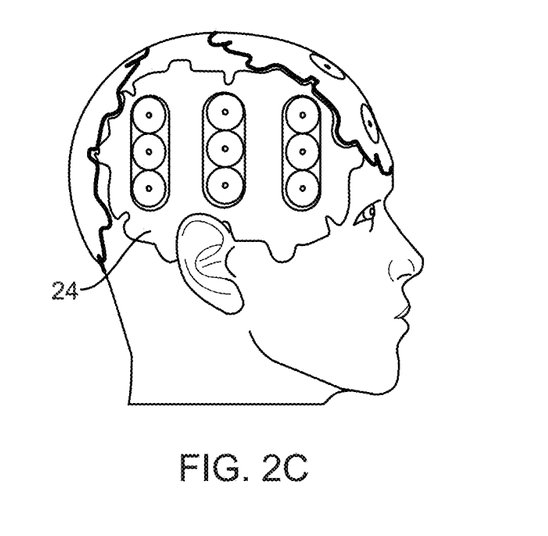
Figure 2D:
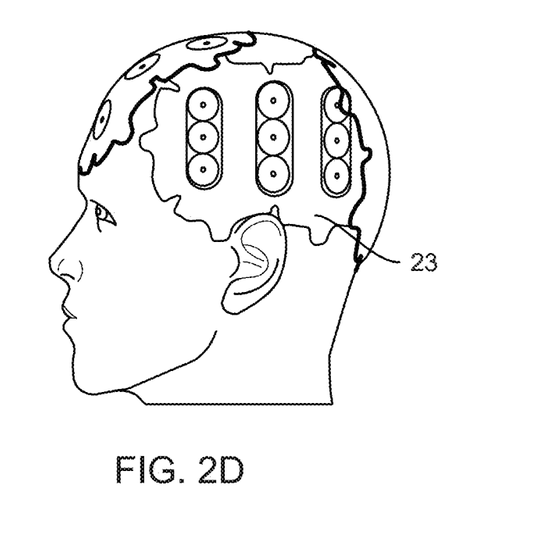

TTFields therapy is a proven approach for treating tumors. FIG. 1 is a schematic representation of the prior art Optune® system for delivering TTFields. The TTFields are delivered to patients via four transducer arrays 21-24 that are placed on the patient's skin in close proximity to a tumor (e.g., as depicted in FIGS. 2A-2D for a person with glioblastoma). The transducer arrays 21-24 are arranged in two pairs, and each transducer array is connected via a multi-wire cable to an AC signal generator 20. The AC signal generator (a) sends an AC current through one pair of arrays 21, 22 during a first period of time, which induces an electric field with a first direction through the tumor; then (b) sends an AC current through the other pair of arrays 23, 24 during a second period of time, which induces an electric field with a second direction through the tumor; then repeats steps (a) and (b) for the duration of the treatment.

Each transducer array 21-24 is configured as a set of capacitively coupled electrode elements E (e.g., a set of 9 electrode elements, each of which is about 2 cm in diameter) that are interconnected via a flex circuit. Each electrode element includes an electrically conductive substrate with a dielectric layer (more specifically, a layer of ceramic material with a high dielectric constant) disposed thereon. Each electrode element is sandwiched between a layer of an electrically conductive medical gel and an adhesive tape. When placing the arrays on the patient, the medical gel conforms to the contours of the patient's skin and ensures good electrical contact of the device with the body. The adhesive tape holds the entire array in place on the patient as the patient goes about their daily activities.

The amplitude of the alternating current that is delivered via the transducer arrays is controlled so that skin temperature (as measured on the skin below the transducer arrays) does not exceed a safety threshold of 41° C. The temperature measurements on the patient's skin are obtained using thermistors T placed beneath some of the disks of the transducer arrays. In the existing Optune® system, each array includes 8 thermistors, with one thermistor positioned beneath a respective disk in the array. (Note that most arrays include more than 8 disks, in which case the temperature measurements are only performed beneath a sub-set of the disks within the array).

The AC signal generator 20 obtains temperature measurements from all 32 thermistors (4 arrays×8 thermistors per array), and the controller in the AC signal generator uses the temperature measurements to control the current to be delivered via each pair of arrays in order to maintain temperatures below 41° C. on the patient's skin. The current itself is delivered to each array via an additional wire (i.e., one wire 28 for each of the arrays 21-24) that runs from the AC signal generator 20 to each array. And an additional wire (not shown) for each of the arrays 21-24 is used as a common return for all 8 thermistors. Thus, each of the four cables that terminate on the arrays 21-24 in the existing Optune system has a total of 10 conductors.

SUMMARY OF THE INVENTION

One aspect of the invention is directed to a first apparatus for applying an alternating electric field to a subject's body. The first apparatus comprises at least four sets of electrode elements, a connector, at least four first conductors, a second conductor, at least four temperature sensors, and a support configured to hold the sets of electrode elements against the subject's body. Each of the sets of electrode elements includes a respective first electrode element and a respective second electrode element disposed in thermal contact with the respective first electrode element. The connector has at least four first pins and a second pin. Each of the at least four first conductors provides an electrically conductive path between (a) a respective one of the first pins and (b) a respective one of the first electrode elements. The second conductor provides an electrically conductive path between the second pin and all of the second electrode elements; and each of the at least four temperature sensors is disposed in thermal contact with a respective one of the sets of electrode elements.

In some embodiments of the first apparatus, within each of the sets of electrode elements, the area of the respective second electrode element is at least double the area of the respective first electrode element.

In some embodiments of the first apparatus, the apparatus has at least nine sets of electrode elements, the connector has at least nine first pins, the apparatus has at least nine first conductors, and the apparatus has at least nine temperature sensors.

In some embodiments of the first apparatus, each of the temperature sensors comprises a thermistor having a first terminal and a second terminal, the connector has a third pin, and each of the first conductors provides an electrically conductive path between (a) a respective one of the first pins, (b) a respective one of the first electrode elements, and (c) the first terminal of a respective thermistor. In these embodiments, the apparatus further comprises a third conductor that provides an electrically conductive path between the third pin and the second terminal of at least one of the thermistors. Optionally, in these embodiments, the second terminals of all the thermistors are wired together.

In some embodiments of the first apparatus, each of the temperature sensors comprises a thermistor having a first terminal and a second terminal, the connector has a third pin, and each of the first conductors provides an electrically conductive path between (a) a respective one of the first pins, (b) a respective one of the first electrode elements, and (c) the first terminal of a respective thermistor. In these embodiments, the apparatus further comprises a third conductor that provides an electrically conductive path between the third pin and the second terminal of at least one of the thermistors. In these embodiments, the thermistors are wired in series, beginning with a first one of the thermistors and ending with a last one of the thermistors. The second terminal of each of the thermistors except for the last thermistor is wired to the first terminal of a respective subsequent thermistor, and the third conductor provides an electrically conductive path between the third pin of the connector and the second terminal of the last thermistor.

In some embodiments of the first apparatus, each of the temperature sensors comprises a region of a pyroelectric material.

In some embodiments of the first apparatus, each of the first electrode elements comprises a conductive plate with a dielectric layer disposed thereon, each of the second electrode elements comprises a conductive plate with a dielectric layer disposed thereon, and the support is configured to hold the first electrode elements and the second electrode elements against the subject's body so that the dielectric layers of the first electrode elements and the dielectric layers of the second electrode elements face the subject's body.

Another aspect of the invention is directed to a second apparatus for applying an alternating electric field to a subject's body using at least four sets of electrode elements, wherein each of the sets of electrode elements includes a respective first electrode element and a respective second electrode element disposed in thermal contact with the respective first electrode element, and wherein each of the sets of electrode elements is disposed in thermal contact with a respective temperature sensor. The second apparatus comprises an AC signal generator that generates an AC output signal. The second apparatus also comprises a connector that includes at least four first pins and a second pin, wherein each of the first pins corresponds to a respective one of the first electrode elements, and wherein the AC output signal is applied to the second pin. The second apparatus also comprises at least four first switches, wherein each of the first switches is configured to selectively either apply or not apply the AC output signal to a respective one of the first pins depending on a state of at least one control signal. The second apparatus also comprises an amplifier configured to accept an input from each of the temperature sensors and generate a corresponding output. And the second apparatus also comprises a controller configured to, based on the output of the amplifier, set the at least one control signal to a state that determines whether the AC output signal is applied or not applied to each of the first pins.

In some embodiments of the second apparatus, the controller is configured to (a) determine, based on the output of the amplifier, when at least one of the first electrode elements is hotter than other first electrode elements and (b) set the at least one control signal to a state that controls the first switches so that the AC signal is not applied to at least one respective first pin.

In some embodiments of the second apparatus, the controller is configured to (a) determine, based on the output of the amplifier, when at least one of the first electrode elements is hotter than a threshold level and (b) set the at least one control signal to a state that controls the first switches so that the AC signal is not applied to at least one respective first pin.

In some embodiments of the second apparatus, the inputs from the temperature sensors arrive via the same first pins that correspond to the first electrode elements.

Another aspect of the invention is directed to a first method of applying an alternating electric field to a subject's body. The first method comprises positioning at least four sets of electrode elements on or in the subject's body, wherein each of the sets of electrode elements has an active area that is adjustable. The first method also comprises energizing each of the sets of electrode elements using its entire active area; measuring a respective temperature of each of the sets of electrode elements; and reducing the active area of at least one of the sets of electrode elements based on a corresponding one of the temperature measurements.

In some instances of the first method, the active area of a given set of electrode elements is reduced when the given set of electrode elements is hotter than other sets of electrode elements. In some instances of the first method, the active area of a given set of electrode elements is reduced when the given set of electrode elements is hotter than a threshold level.

Another aspect of the invention is directed to a second method of applying an alternating electric field to a subject's body. The second method comprises positioning at least four sets of electrode elements on or in the subject's body, wherein each of the sets of electrode elements has an active area that is adjustable. The second method also comprises energizing each of the sets of electrode elements using its entire active area; measuring a respective temperature of each of the sets of electrode elements; and reducing the active area of at least one of the sets of electrode elements based on a corresponding one of the temperature measurements. The positioning comprises positioning at least four first electrode elements on or in the subject's body and positioning at least four second electrode elements on or in the subject's body. Each of the first electrode elements is wired so that it can be energized independently of the other first electrode elements. Each of the second electrode elements is positioned adjacent to and in thermal contact with a respective one of the first electrode elements. The second electrode elements are wired together so that all of the second electrode elements must be either collectively energized or collectively not energized. The energizing comprises energizing the first electrode elements and all of the second electrode elements. The reducing of the active area comprises deenergizing selected ones of the first electrode elements based on a respective temperature measurement.

In some instances of the second method, the deenergizing of a given first electrode element occurs when the given first electrode element is hotter than other first electrode elements.

In some instances of the second method, the deenergizing of a given first electrode element occurs when the given first electrode element is hotter than a threshold level.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Although the FIG. 1 approach described above is very effective for delivering TTFields to a tumor, the effectiveness of the treatment will drop if good electrical contact is not maintained between each of the elements in the four transducer arrays 21-24 and the person's body. This can happen, for example, if the hydrogel beneath one or more elements of the transducer arrays dries out over time, or due to hair growth beneath one or more of the elements.

Assume, for example, that there are 9 electrode elements E in each of the transducer arrays 21-24, that the hydrogel beneath a single electrode element E on the front transducer array 21 has dried out; and that enough hydrogel is present beneath (a) all the other electrode elements E of that transducer array 21, and (b) all the electrode elements E of the other transducer arrays 22-24. In this situation, the resistance between the single electrode element E and the person's body will be higher than the resistance between any of the other electrode elements and the person's body. And this increase in resistance will cause the temperature of the single electrode element E to rise more than the other electrode elements.

In this situation, because all of the electrode elements E in each of the transducer arrays 21-24 are wired in parallel, the AC signal generator 20 must limit the current that is applied to the entire front/back pair of transducer arrays 21, 22 in order to keep the temperature of the single electrode element E on the front array 21 below 41°, even though the temperature at all the remaining electrode elements E on the front and back transducer arrays 21, 22 may be well below 41° C. And this decrease in current causes a corresponding decrease in the strength of the electric field at the tumor, which can reduce the efficacy of the treatment.

One possible approach for dealing with this situation is to wire a separate conductor to each of the 9 electrode elements (as opposed to the prior art approach of wiring all of the electrode elements together in parallel). If this approach is implemented, it becomes possible to switch off the AC signal to whichever electrode element is overheating without switching off the AC signal to the other electrode elements on the same array. This approach is referred to herein as the "individually addressable electrode approach."

But switching an electrode element completely off using the individually addressable electrode approach can cause the current that passes through the remaining electrode elements to increase, which would raise their temperature. In addition, switching an electrode element completely off could have a negative impact on the distribution of the electric field within the subject's body. Moreover, the inventor has determined that in the vast majority of situations, a current reduction of less than 20% will prevent any given electrode element from overheating. As a result, switching an electrode element completely off using the individually addressable electrode approach could be considered to be overkill. The embodiments described below obviate or minimize the problems identified in this paragraph by replacing each of the prior art electrode elements with a set of electrode elements.

Figure 3:
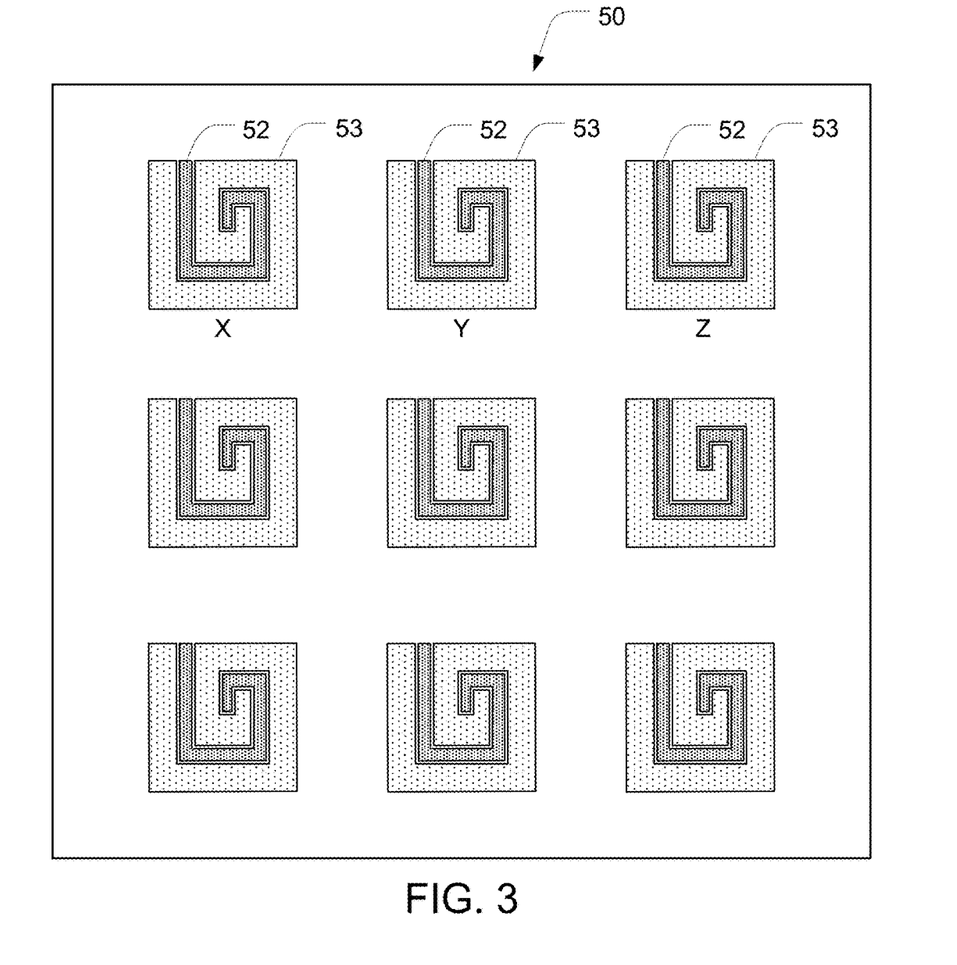
FIG. 3 is a schematic representation of a transducer array that is used for applying TTFields to a subject's body.

FIG. 3 is a schematic representation of a transducer array 50 that includes nine sets 52/53 of electrode elements that are used for applying TTFields to a subject's body. Each set includes a first electrode element 52 and a second electrode element 53 that are disposed in thermal contact with each other. The overall array 50 includes at least four sets 52/53 of first and second electrode elements (e.g., nine sets 52/53 in the embodiment illustrated in FIG. 3, or another number between 4 and 50). A separate first conductor is wired to each of the first electrode elements 52, which makes it possible to switch the AC signal to any given one of the first electrode elements 52 on or off independently. But all of the second electrode elements 53 are wired in parallel to a second conductor, which means that whenever an AC signal is applied to the second conductor, the AC signal will reach all of the second electrode elements 53.

In some preferred embodiments, the second electrode element 53 within any given set is at least double the area of the respective first electrode element 51. Assume, for purposes of discussion, that within any given set of electrode elements 52/53, 70% of the total area is occupied by the second electrode element 53, and 30% of the total area is occupied by the first electrode element 52. When delivering TTFields, the current that passes through any given set 52/53 of electrode elements is related to the active area of that set. As a result, when a given AC voltage is applied to both the first electrode element 52 and the second electrode element 53, a full measure of current (i.e., 100%) will pass through the set 52/53. But when the same AC voltage is applied to only the second electrode element 53 and not to the first electrode element 52, the current that passes through the entire set 52/53 will drop from 100% to a lower level (e.g., 80%).

Assume that an AC voltage is applied to the second electrode element 53 during an interval of time (e.g., a 1 second interval of time) via the second conductor. Further assume that during this same interval of time, the same AC voltage is applied to the first electrode element 52 in the set of electrode elements 52/53 labeled X (via a corresponding first conductor), but the AC voltage is not applied to the first electrode element 52 in the set of electrode elements 52/53 labeled Z. In this situation, because current is related to the active area, a full measure of current (i.e., 100%) will pass through the set 52/53 labeled X, but a lower current will pass through the second set 52/53 labeled Z.

The first electrode element 52 and a second electrode element 53 within any given set 52/53 are shaped and positioned so as to be in thermal contact with each other (i.e., they are shaped and positioned so that heating up the first electrode element 52 will cause the second electrode element 53 to heat up, and vice versa). Note that the thermal contact between the first electrode element 52 and the second electrode element 53 may be indirect thermal contact, with intervening components disposed between the first electrode element 52 and the second electrode element 53. One preferred approach for achieving thermal contact between the first and second electrode elements 52, 53 within any given set is to shape those electrode elements 52, 53 as interleaved spirals (not shown) or as interleaved squared-off spirals (as depicted in FIG. 3). In alternative embodiments, different interleaved patterns may be used (e.g., interleaved stripes or interleaved comb-shaped patterns). Interleaving the first and second electrode elements 52, 53 in this matter will improve the thermal contact between the first and second electrode elements 52, 53, which will minimize the variation in temperature between those elements.

A temperature sensor is disposed in thermal contact with each set 52/53 of electrode elements. (Here again, the thermal contact may be indirect.) Preferably, the number of temperature sensors matches the number of sets of electrode elements. For example, when four sets 52/53 of electrode elements are used, there will be four temperature sensors. In some embodiments, thermistors are used as the temperature sensors.

Figure 4A:
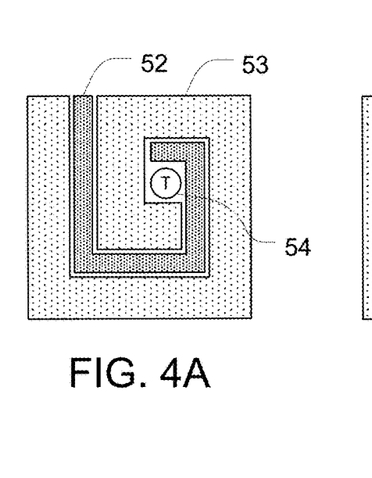
FIG. 4A-4C depict three respective approaches for positioning temperature sensors in thermal contact with the electrode elements in a transducer array.
Figure 4B:
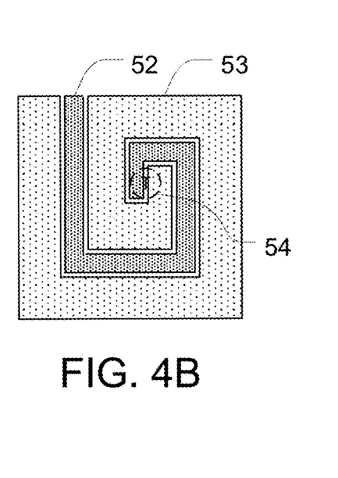

FIG. 4A depicts a first approach for positioning the temperature sensor (e.g., a thermistor 54) in thermal contact with the first and second electrode elements 52, 53. In this approach, a thermistor 54 is positioned in an open space between the first and second electrode elements 52, 53 within each set 52/53, so that the thermistor 54 is disposed in thermal contact with both the first and second electrode elements 52, 53. FIG. 4B depicts a second approach for positioning the temperature sensor. In this approach, the first and second electrode elements 52, 53 occupy almost the entire area of the set 52/53, and a thermistor 54 is positioned on a backside of the set 52/53, so that the thermistor 54 is disposed in thermal contact with both the first and second electrode elements 52, 53. This approach is particularly well suited in cases where the first and second electrode elements 52, 53 are implemented using respective traces of a flex circuit. Two approaches for using a set of thermistors as the temperature sensors are described below in connection with FIGS. 5-8.

Figure 4C:
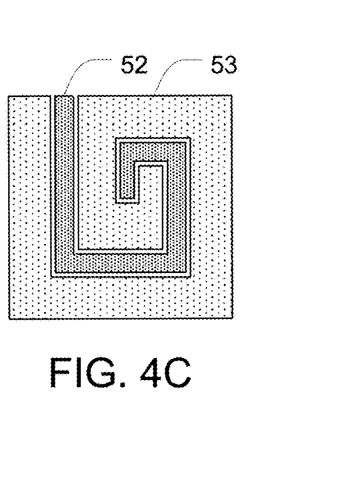

FIG. 4C depicts a third approach for positioning the temperature sensor. In this approach, the first and second electrode elements 52, 53 occupy almost the entire area of the set 52/53, and temperature-sensing is implemented by positioning regions of a pyroelectric material (not shown) behind and in thermal contact with both the first and second electrode elements 52, 53. This approach is also particularly well suited in cases where the first and second electrode elements 52, 53 are implemented using respective traces of a flex circuit. A description of how to use regions of pyroelectric material to sense temperature is provided below.

The embodiments described herein advantageously provide the ability to reduce the current that flows through a given area of a transducer array 50, without completely shutting off the current that flows through the given area.

One approach for controlling the current that passes through each area of a transducer array is to (1) start off with the prior art configuration depicted in FIG. 1; (2) reconfigure each of the electrode elements E to resemble the shape of the second electrode elements 53 depicted in FIG. 3; (3) add nine additional electrode elements that are shaped like the first electrode elements 52 depicted in FIG. 3 and interleaved with the original electrode elements E; and (4) add an additional conductor that runs to each of the new electrode elements so that the new electrode elements can be energized individually. While this approach is workable, it requires almost double the number of conductors in each of the cables that runs to the transducer arrays. For example, in transducer arrays that have 9 controllable areas, a total of 20 wires would be needed in each cable (i.e., 1 to provide common access to all of the original electrode elements, 9 to provide individual access to each of the 9 new electrode elements, an additional 9 for the signals from the thermistors, plus one additional wire to serve as a common return for all 9 thermistors). And this significant increase in the number of wires in each cable tends to make the cables less flexible and more cumbersome, which can make the system harder to use, and reduce patient compliance.

The embodiments described below advantageously provide the ability to control the current that is routed through individual areas of the transducer array 50, without unduly increasing the number of conductors in the cables that terminate on the transducer arrays. These embodiments can be used to implement systems that distribute the functions of outputting current (in order to generate TTFields) and obtaining temperature readings into mutually exclusive time slots or phases. In these systems, because temperature readings are not obtained at the exact same instant of time while the transducer arrays are outputting current, the same set of conductors can be used to output current and to input temperature readings. This advantageously reduces the total number of conductors that must be included in each cable.

One suitable approach for distributing the functions of outputting current and obtaining temperature readings into mutually exclusive time slots or phases is to (i) output current for an interval of time (e.g., 1 s) and then turn the current off, then (ii) spend a short period of time (e.g., 10 ms) obtaining temperature measurements, and then repeating those two steps (i) and (ii) in an alternating sequence repeatedly (e.g., for 12-18 hours per day). The operation of the system during each of those phases (i.e., the current-outputting phase and the temperature-reading phase) is described below for a variety of embodiments.

Figure 5:
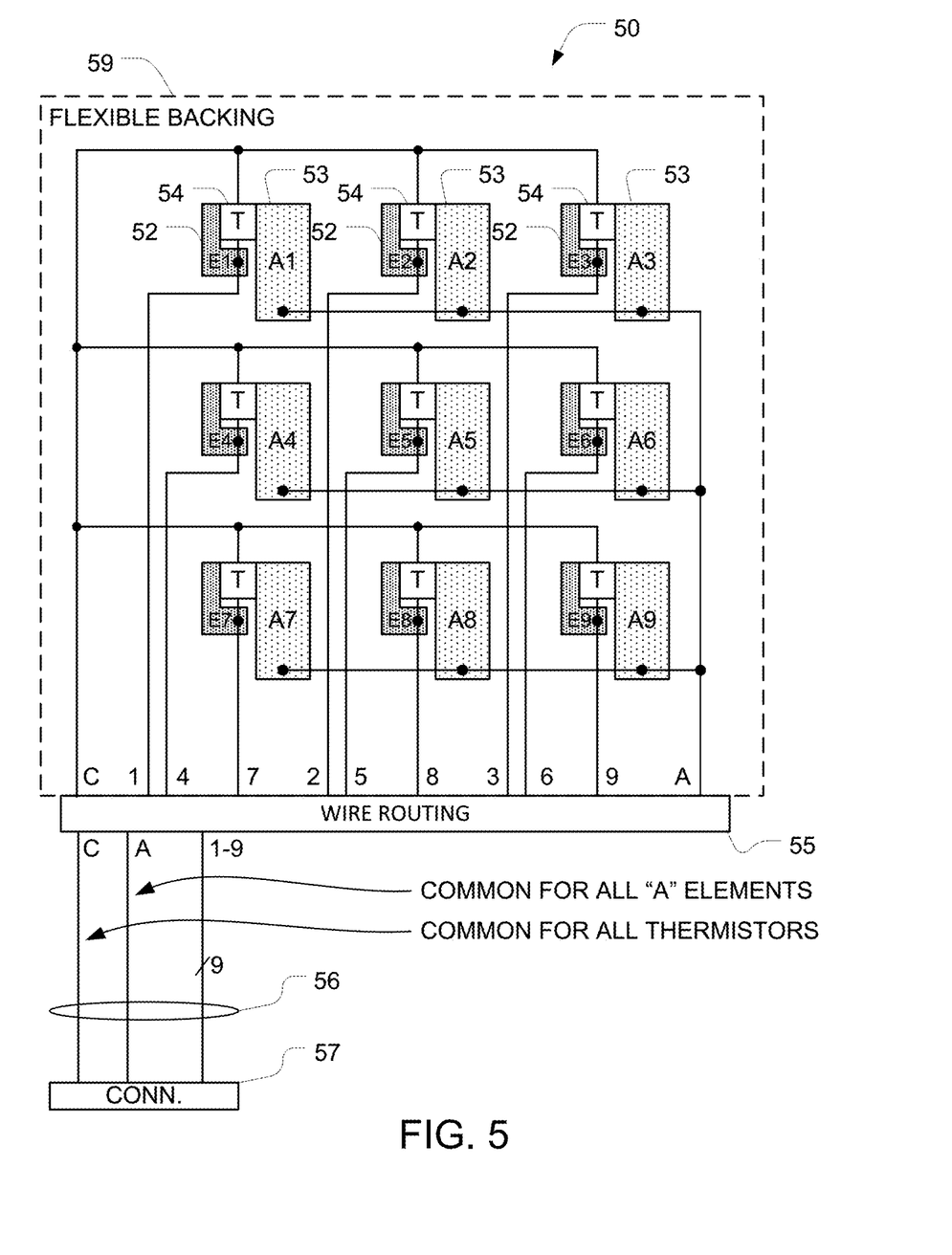
FIG. 5 depicts a transducer array that provides individual control over the current that passes through nine different areas of the transducer array.

FIG. 5 is a schematic representation of a first embodiment of a transducer array 50 that provides individual control over the current that passes through nine different areas of the transducer array 50 during the current-outputting phase. As will be described below in connection with FIG. 6, four copies of the transducer array 50 are preferably used to administer TTFields treatment to a person's head (or other body part).

Each transducer array 50 includes at least four sets 52/53 of electrode elements. Each set 52/53 includes a respective first electrode element 52 and a respective second electrode element 53 disposed in thermal contact with each other. The first electrode elements 52 are labeled E1-E9 and the second electrode elements 53 are labeled A1-A9 for ease of reference in the FIG. 5 embodiment. The shape and positioning of the first and second electrode elements 52, 53 with respect to each other is as described above in connection with FIGS. 3-4. (Note that the shape and positioning is not depicted in FIG. 5 to make it easier to see the electrical interconnections between the various components.) Each set 52/53 of electrode elements is positioned at a different area of the transducer array 50, and the first and second electrode elements 52, 53 within any given set are positioned in thermal contact with each other.

Each of the first and second electrode elements 52, 53 has an electrically conductive substrate with a dielectric layer disposed thereon. The electrically conductive substrate may be implemented using a thin layer of metal. The dielectric layer may be implemented using a ceramic material or a layer of a polymer with a high dielectric constant (e.g., at least 20).

In the embodiment depicted in FIG. 5, all of the first and second electrode elements 52, 53 are held in place by a support structure 59. The support structure is configured to hold the electrode elements against the subject's body so that the dielectric layer of the first and second electrode elements 52, 53 faces the subject's body and can be positioned in contact with the subject's body. Optionally, this support structure may comprise a flexible backing 59 (e.g., a layer of foam material). Preferably, a layer of hydrogel is disposed between the dielectric layer of the first and second electrode elements 52, 53 and the subject's body when the transducer array 50 is placed against the subject's body. Construction of the support structure 59 may be implemented using any of a variety of conventional approaches that will be apparent to persons skilled in the relevant arts, including but not limited to self-adhesive fabric, foam, or plastic sheeting.

Each transducer array 50 also has a connector 57 that is used to send electrical signals into and out of the transducer array 50. The connector 57 has at least four first pins and a second pin. In the illustrated embodiment, the number of first pins is the same as the number of first electrode elements 52, and each of the first pins corresponds to a respective one of those first electrode elements 52. And in the illustrated embodiment, there is only a single second pin, labeled A. Note that as used herein, the term "pin" can refer to either a male or female pin of the connector 57.

Each of the first electrode elements 52 (labeled E1-E9) is wired via a respective individual first conductor to a respective first pin of the connector 57. More specifically, each of the first conductors provides an electrically conductive path between (a) a respective one of the first pins in the connector 57 and (b) the conductive substrate of a respective one of the first electrode elements 52 (E1-E9). These first conductors are numbered 1-9 just above the "wire routing" block 55 (which funnels the individual conductors together into a single cable 56). In some preferred embodiments, the electrical connection to each of the first electrode elements 52 comprises one or more traces on a flex circuit and/or one or more conductive wires.

Because the connector 57 has an individual first pin that corresponds to each of the individual first electrode elements 52, and because an electrically conductive path exists between each of the first pins and a respective one of the first electrode elements 52, the system that mates with the connector 57 can selectively energize or not energize each of the first electrode elements 52 individually by either applying or not applying an AC signal to the respective first pin on the connector 57. In contrast, all of the second electrode elements 53 (labeled A1-A9) are connected via an electrically conductive path (e.g., wired together in series or parallel) to the node labeled "A" which eventually terminates on a second pin of the connector 57. As a result, the system that mates with the connector 57 must selectively energize or not energize all of the second electrode elements 53 together by either applying or not applying an AC signal to the second pin on the connector 57.

Therefore, when the system that mates with the connector 57 is applying an AC signal to the second pin on the connector 57, any given individual area of the transducer array 50 will either (a) pass a full level of current (i.e., when the respective first electrode element 52 is energized) or (b) pass a lower level of current (i.e., when the respective first electrode element 52 is not energized). This advantageously provides the ability to reduce the current that flows through a given area of a transducer array 50 without completely shutting off the current that flows through that area.

We shall now discuss operation of the FIG. 5 embodiment during the temperature-reading phase. Each transducer array 50 also includes at least four temperature sensors, each of which is disposed in thermal contact with a respective one of the sets 52/53 of electrode elements. In the embodiment illustrated in FIG. 5, the temperature sensors are implemented using thermistors 54, with one thermistor positioned with respect to each set 52/53 so that the thermistor 54 can sense the temperature of the first and second electrode elements 52, 53 within that set. This may be accomplished, for example, using any of the approaches described above in connection with FIGS. 4A-4B. Each of the thermistors 54 has a first terminal (i.e., the lower terminal of the thermistor in FIG. 5) and a second terminal (i.e., the upper terminal of the thermistor in FIG. 5).

In this embodiment, each of the first conductors provides an electrically conductive path between (a) a respective one of the first pins in the connector 57, (b) the conductive substrate of a respective one of the first electrode elements 52 (E1-E9), and (c) the first terminal of the corresponding thermistor 54.

In the FIG. 5 thermistor-based embodiment, each transducer array 50 has a third conductor that provides an electrically conductive path between a third pin of the connector 57 (labeled C in FIG. 5) and the second terminal (i.e., the upper terminal in FIG. 5) of at least one of the thermistors 54. In the embodiment depicted in FIG. 5, the second terminal of all of the thermistors are wired together. In this embodiment, the third conductor provides an electrically conductive path between the third pin of the connector 57 and the second terminal of all of the thermistors 54. The third conductor may optionally be implemented using a plurality of segments of wire and/or a plurality of traces on a flex circuit.

Because the connector 57 has an individual first pin that corresponds to the first terminal of each of the thermistors 54 and because an electrically conductive path exists between each of the first pins and a respective one of the thermistors 54, the system that mates with the connector 57 has access to the first terminal of each of the thermistors 54. In addition, because the second terminal of all the thermistors 54 are all wired together and connected to the third pin (labeled C), the system that mates with the connector 57 also has access to the second terminal of each of the thermistors 54. As a result, the system that mates with the connector 57 can measure the resistance of any of the thermistors 54 during the temperature-reading phase. This may be accomplished, for example, by routing a known current through each thermistor 54 and measuring the voltage that appears across each thermistor.

Notably, because any given first pin on the connector 57 corresponds to a respective one of the individual first electrode elements 52 (during the current-outputting phase) and also corresponds to a respective one of the individual thermistors 54 (during the temperature-reading phase), each of the first pins on the connector 57 serves two functions. This reduces the number of wires that must be included in each of the cables 56, which in turn advantageously makes the cables more flexible and less cumbersome.

Figure 6:
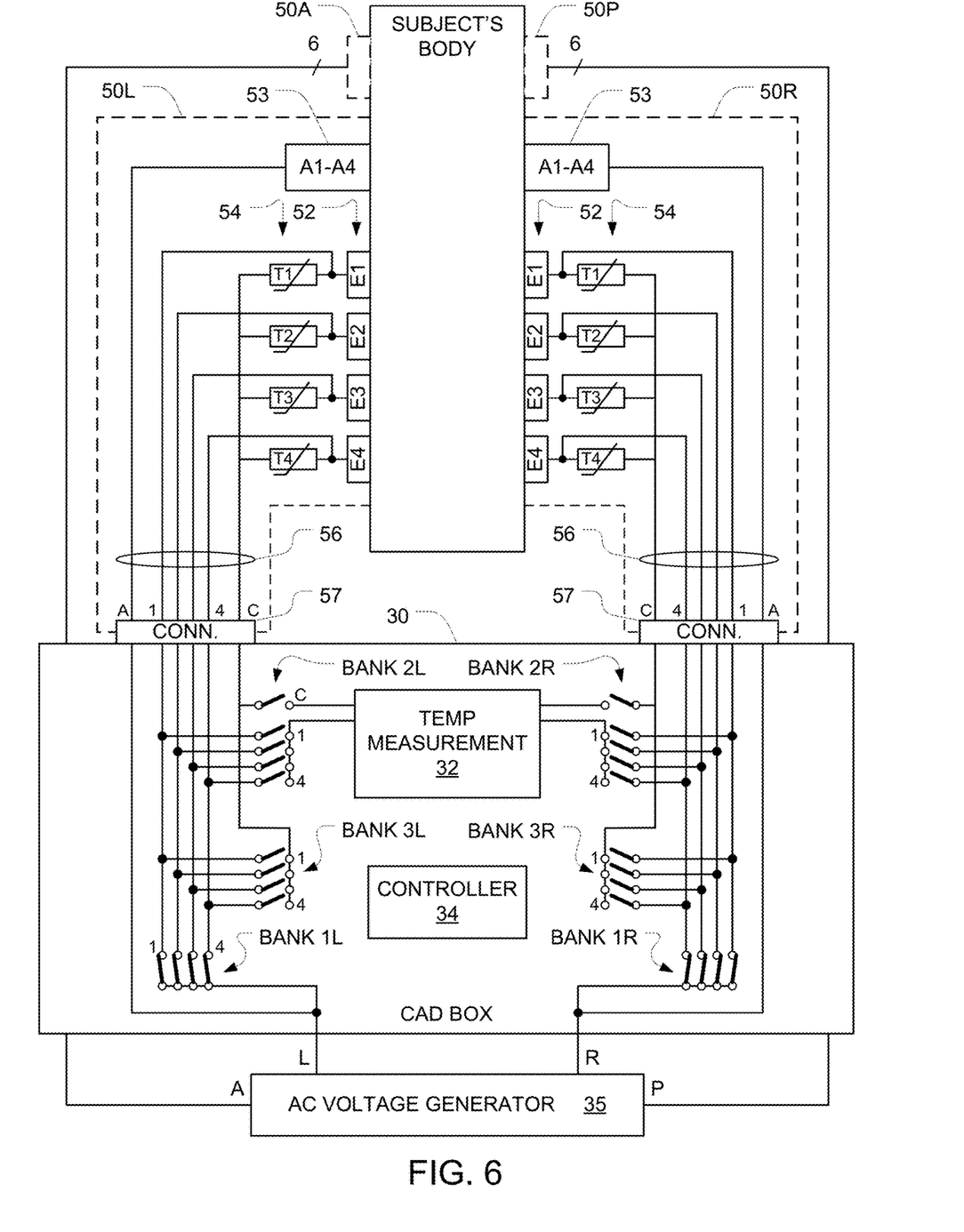
FIG. 6 is a block diagram of a system that uses four copies of the FIG. 5 transducer array to apply TTFields to a subject.

FIG. 6 is a block diagram of a system that uses four copies of the transducer array 50 (described above in connection with FIG. 5) to apply TTFields to a subject. In FIG. 6, these four copies are labeled 50A, 50P, 50L, and 50R, where A, P, L, and R stand for anterior, posterior, left, and right, respectively. The lower portion of FIG. 6 depicts an AC voltage generator 35 and a "CAD box" 30 as separate blocks, the latter of which includes a temperature measurement block 32, a controller 34, and banks of switches 1L, 2L, 3L, 1R, 2R, and 3R. In some embodiments, the components in those two blocks 35, 30 may be physically divided into two separate housings. But in alternative embodiments, the components in those two blocks 35, 30 are combined into a single housing.

For clarity, only the left and right channels are depicted in FIG. 6. But the remaining channels (i.e., the anterior and posterior channels) operate in the same way as the left and right channels, respectively. Additionally, each of the transducer arrays 50 in FIG. 6 is depicted with only 4 first electrode elements 52 and four thermistors 54 for clarity. But it is expected that practical systems will have a larger number (e.g., between 9 and 30) of first electrode elements and thermistors, and will also have a larger number of certain other components (e.g., switches, conductors, etc.), depending on the number of first electrode elements 52 that are actually used in each of the transducer arrays 50.

The FIG. 6 system can measure the temperatures of the thermistors 54 in the left channel 50L during the temperature-reading phase by controlling the electronically-controlled switches in bank 2L (which may be implemented using bidirectional analog switches) to select each of the thermistors in turn. For example, switch C and switch 1 should be closed to select thermistor T1; switch C and switch 2 should be closed to select thermistor T2; etc. After any given one of the thermistors T1-T4 within the transducer array 50L has been selected, the temperature measurement block (TMB) 32 can determine the temperature of the thermistor by measuring the resistance of the thermistor. This may be accomplished, for example, by using a current source that generates a known current (e.g., 150 µA) positioned within the TMB 32, so that the known current will be routed into whichever thermistor is selected by the bank of switches 2L at any given instant. The known current will cause a voltage to appear across the selected thermistor (T1-T4), and the temperature of the selected thermistor can be determined by measuring this voltage. A controller 34 runs a program that selects each of the thermistors T1-T4 in turn and measures the voltage that appears across each of the thermistors (which is indicative of the temperature at the selected thermistor) in turn. An example of suitable hardware and procedures that may be used to obtain temperature readings from each of the thermistors is described in US 2018/0050200, which is incorporated herein by reference in its entirety.

Measuring the temperature of the thermistors 54 in the right channel 50R is accomplished using the same approach described above in connection with the left channel 50L, except that the bank of switches 2R is used instead of bank 2L. Corresponding banks of switches (not shown) are also provided for the other channels 50A, 50P, and a similar approach is used in those channels as well.

Assume that within a given interval of time (e.g., 1 second) during the current-outputting phase, the AC voltage generator 35 is applying an AC signal between the L and R terminals. This AC signal is applied to the A terminals of the left and right transducer arrays 50L, 50R, which means that the output of the AC voltage generator is applied to all of the second electrode elements 53 (A1-A4). Based on the temperature readings obtained from the thermistors 54 (T1-T4) during the temperature-reading phase, the controller 34 controls the switches in bank 1L to either turn on or turn off the current (which originates in the AC voltage generator 35) to each of the corresponding first electrode elements 52 (E1-E4) during the next current-outputting phase. For example, to leave the full current on for all four of the sets 52/53, all four of the switches in bank 1L should be closed. To reduce the current that passes through the E1/A1 set 52/53 of electrode elements (see FIG. 5), switch 1 in bank 1L should be opened; and to reduce the current that passes through the E2/A2 set 52/53 of electrode elements, switch 2 in bank 1L should be opened; etc.

Controlling the current that is routed through individual first electrode elements during the current-outputting phase can therefore be used to reduce the current that passes through a given area when that area begins to get hot. This can advantageously prevent overheating without completely turning off the current that passes through a given area.

In some embodiments, the controller 34 may be programmed to keep the temperature at all of the areas below a safety threshold (e.g., below 41° C.) as follows: Begin by closing all of the switches 1-4 in bank 1L, so that a full measure of current (i.e., 100%) passes through each set 52/53 of electrode elements during the current-outputting phase. Then, during the temperature-reading phase, based on signals arriving via the TMB 32, the controller 34 determines whether the temperature at each of the areas exceeds an upper threshold (e.g., 40° C.) that is below the safety threshold. When the controller 34 detects this condition, the controller 34 reduces the current that passes through the warmer areas by switching off the signal to the first electrode element 52 within those areas during the next current-outputting phase. Notably, this procedure only lowers the current that passes through certain areas of the transducer array 50, and does not lower the current that passes through the remaining areas on that transducer array 50.

Optionally, the decision by the controller 34 to turn off a given first electrode element 52 may be based on the speed at which the corresponding thermistor 54 heats up (as measured via the temperature sensors 54 and the TMB 32 during two or more temperature-reading phases that are spaced in time). More specifically, if the controller 34 recognizes that a given thermistor 54 is heating up faster than expected, the controller 34 can proactively open the switch that feeds the corresponding first electrode element 52 during subsequent current-outputting phases.

Optionally, the controller 34 can control the current that passes through any given area on the transducer array 50 based on real-time temperature measurements. For example, if the temperature at a given area reaches 40° C., the controller 34 can open the switch that feeds the corresponding first electrode element 52, which will reduce the current that passes through the corresponding area during the current-outputting phase. The controller 34 then waits until the temperature measured using the temperature sensors 54 drops below a second temperature threshold (e.g., below 38° C.). Once the temperature drops below this second temperature threshold, the controller 34 can close the switch that feeds the corresponding first electrode element 52, which will restore the current that passes through the corresponding area during the current-outputting phase to its original value.

Individually switching the current to each of the first electrode elements 52 in the right channel 50R is accomplished using the same approach described above in connection with the left channel 50L, except that the bank of switches 1R is used instead of bank 1L. Corresponding banks of switches (not shown) are also provided for the other channels 50A, 50P, and a similar approach is used in those channels as well.

In some preferred embodiments, the AC signal generator 35 (a) sends an AC current through the anterior/posterior arrays 50A/50P during a first period of time (e.g., 1 sec.), which induces an electric field with a first direction through the tumor in the subject's body; then (b) sends an AC current through the left/right arrays 50L/50R during a second period of time (e.g., 1 sec.), which induces an electric field with a second direction through the tumor; then repeats steps (a) and (b) for the duration of the treatment. In these embodiments, the controller 34 may decide whether to switch each of the first electrode elements 52 on or off just prior to each 1 sec. interval of time.

Optionally, an additional bank of switches 3L may be provided. Each of the switches in this bank is wired in parallel with a corresponding one of the thermistors T1-T4, so that when a given one of the switches 1-4 is closed, a respective one of the thermistors T1-T4 will be shorted out.

The reason for including the additional bank of switches 3L is that when (a) current from the AC voltage generator 35 is flowing through the first electrode elements 52 of the left channel 50L, the subject's body, and the first electrode elements 52 of the right channel 50 during the current-outputting phase, and (b) the power to any of the first electrode elements 52 of the left channel 50L is switched off by a corresponding one of the switches in bank 1L, current can sneak through the thermistors 54 in the left channel 50L. Assume, for example, that only switch #2 in bank 1L is switched off (i.e., open). Because switches #1, 3, 4 are switched on (i.e., closed), the AC voltage generator 35 will impose a voltage on electrode elements E1, E3, E4. Thermistors T1 and T2 provide a path for current to flow from E1 to E2; thermistors T3 and T2 provide a path for current to flow from E3 to E2; and thermistors T4 and T2 provide a path for current to flow from E4 to E2. This is equivalent to the parallel combination of E1, E3, and E4 wired in series with E2. Because the number of thermistors in this parallel combination increases linearly with the number of first electrode elements 52, the current in the single thermistor E2 (which is wired in series with the parallel combination) can become significant. Including the optional additional bank of switches 3L provides the system with the ability to prevent power dissipation in that single thermistor E2 by closing the corresponding switch #2 in bank 3L.

To accomplish this (in those embodiments that include the additional bank of switches 3L), the controller 34 may be programmed so that any time a given one of the switches in bank 1L is opened, the corresponding switch in bank 3L is closed. This will prevent the thermistor 54 associated with the switched-off first electrode element 52 from dissipating too much power, as described in the previous paragraph.

In those embodiments that include the additional bank of switches 3L, individual bypassing of each of the thermistors 54 in the right channel 50R is accomplished using the same approach described above in connection with the left channel 50L, except that the bank of switches 3R is used instead of bank 3L. Corresponding banks of switches (not shown) are also provided for the other channels 50A, 50P, and a similar approach is used in those channels as well.

Figure 7:
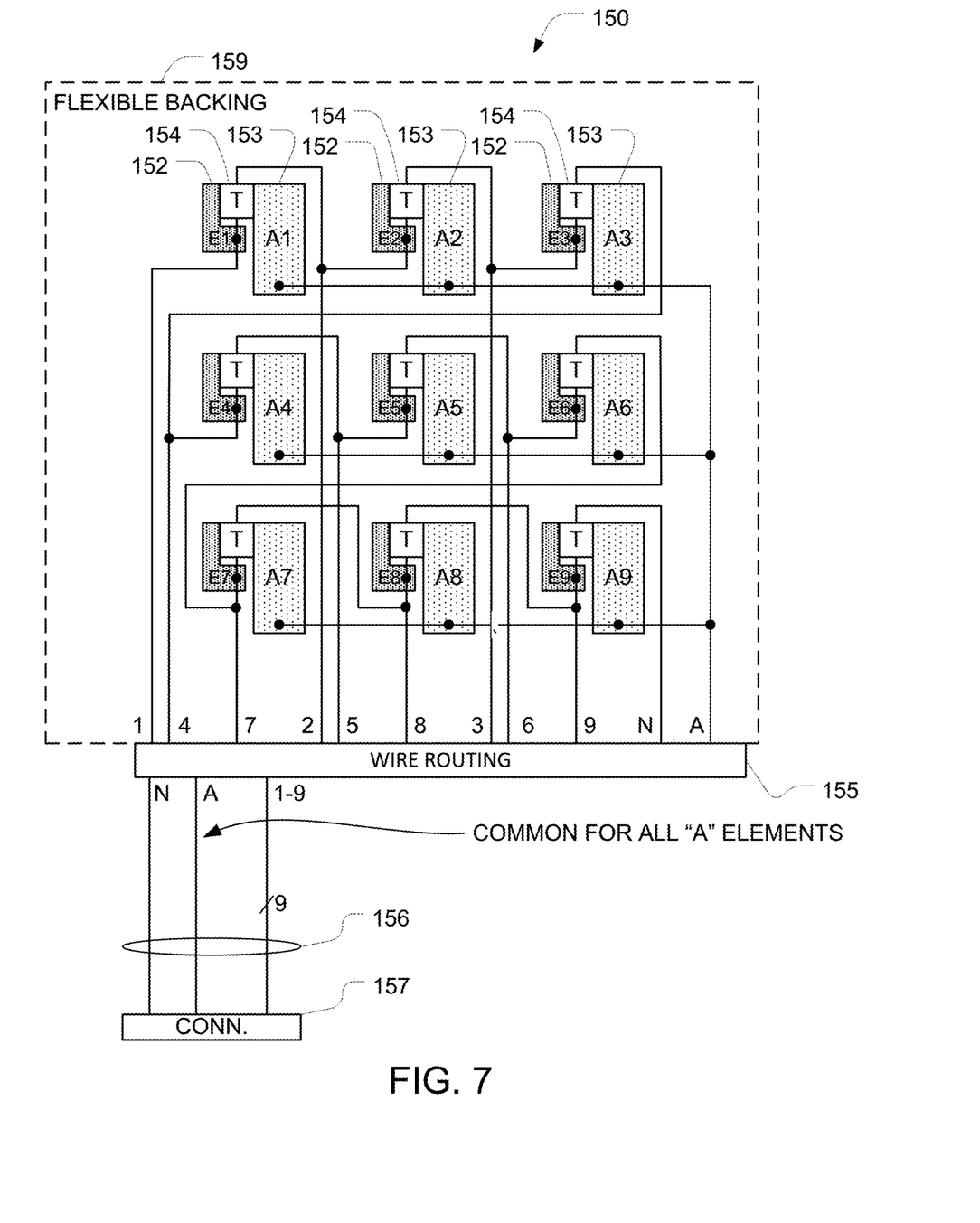
FIG. 7 depicts another transducer array that provides individual control over the current that passes through nine different areas of the transducer array.

FIG. 7 depicts a second embodiment of a transducer array 150 that provides individual control over the current that passes through nine different areas of the transducer array 150 during the current-outputting phase. As will be described below in connection with FIG. 8, four copies of the transducer array 150 are preferably used to administer TTFields treatment to a person's head (or other body part).

Each transducer array 150 includes at least four sets 152/153 of electrode elements. Each set 152/153 includes a respective first electrode element 152 and a respective second electrode element 153 disposed in thermal contact with each other. The first electrode elements 152 are labeled E1-E9 and the second electrode elements 153 are labeled A1-A9 for ease of reference. The first and second electrode elements 152, 153 are similar, respectively, to the first and second electrode elements 52, 53 of the FIGS. 5-6 embodiment described above. Each set 152/153 of electrode elements is positioned at a different area of the transducer array 150, and the first and second electrode elements 152, 153 within any given set are positioned in thermal contact with each other.

The first and second electrode elements 152, 153 are held in place by a support structure 159, which is similar to the support structure 59 in the FIG. 5 embodiment.

Each transducer array 150 also has a connector 157 that is used to send electrical signals into and out of the transducer array 150. The connector 157 has at least four first pins and a second pin. In the illustrated embodiment, the number of first pins is the same as the number of first electrode elements 152, and each of the first pins corresponds to a respective one of those first electrode elements 152. And in the illustrated embodiment, there is only a single second pin, labeled A. Note that as used herein, the term "pin" can refer to either a male or female pin of the connector 157.

Each transducer array 150 also has at least four first conductors, and the number of these first conductors will depend on the number of first electrode elements 152. For example, in the embodiment depicted in FIG. 7, which contains 9 first electrode elements 152, there are 9 first conductors. Each of these first conductors provides an electrically conductive path between (a) a respective one of the first pins in the connector 157 and (b) the conductive substrate of a respective one of the first electrode elements 152 (E1-E9). These first conductors are labeled 1-9 just above the "wire routing" block 155 (which funnels the individual conductors together into a single cable 156). As in the FIG. 5 embodiment, each of these first conductors may optionally be implemented using a plurality of segments of wire and/or a plurality of traces on a flex circuit.

As in the FIG. 5-6 embodiment, the system that mates with the connector 157 can selectively energize or not energize each of the first electrode elements 152 individually by either applying or not applying an AC signal to the respective first pin on the connector 157 during the current-outputting phase. But because all of the second electrode elements 153 are wired together, it must selectively energize or not energize all of the second electrode elements 153 together by either applying or not applying an AC signal to the second pin on the connector 157. Therefore, any given individual area of the transducer array 150 will either (a) pass a full level of current (i.e., when the respective first electrode element 152 is energized) or (b) pass a lower level of current (i.e., when the respective first electrode element 152 is not energized).

We shall now discuss operation of the FIG. 7 embodiment during the temperature-reading phase. Each transducer array 150 also includes at least four temperature sensors, each of which is disposed in thermal contact with a respective one of the sets 152/153 of electrode elements. As in the FIG. 5-6 embodiment, the temperature sensors may be implemented using thermistors 154. Each of the thermistors 154 has a first terminal (i.e., the lower terminal of the thermistor in FIG. 7) and a second terminal (i.e., the upper terminal of the thermistor in FIG. 7). In these embodiments, each of the first conductors provides an electrically conductive path between (a) a respective one of the first pins in the connector 157, (b) the conductive substrate of a respective one of the first electrode elements 152 (E1-E9), and (c) the first terminal of the corresponding thermistor 154.

Notably, the plurality of thermistors 154 in this FIG. 7 embodiment are arranged in series, beginning with a first one of the thermistors (i.e., the top left in FIG. 7) and ending with a last one of the thermistors (i.e., the bottom right in FIG. 7). The second terminal of each of the thermistors except for the last thermistor is wired to the first terminal of a respective subsequent thermistor.

Each transducer array 150 has a third conductor that provides an electrically conductive path between the third pin of the connector 157 and the second terminal of the last thermistor 154 (i.e., the upper terminal of the bottom right thermistor in FIG. 7). The third conductor may optionally be implemented using a plurality of segments of wire and/or a plurality of traces on a flex circuit.

Because the connector 157 has an individual first pin that corresponds to each of the individual first electrode elements 152, and because an electrically conductive path exists between each of the first pins and a respective one of the first electrode elements 152, the system that mates with the connector 157 can selectively energize or not energize each of the first electrode elements 152 individually by either applying or not applying a signal to the respective first pin on the connector 157 during the current-outputting phase. And because the two terminals of any given one of the thermistors 154 are wired to different pins on the connector 157, the system that mates with the connector 157 has access to both terminals of each of the thermistors 154. As a result, the system that mates with the connector 157 can measure the resistance of any of the thermistors 154 during the temperature-reading phase.

Notably, because any given first pin on the connector 157 corresponds to a respective one of the individual first electrode elements 152 (during the current-outputting phase) and also corresponds to a respective one or two of the individual thermistors 154 (during the temperature-reading phase), each of the first pins on the connector 157 serves two functions. This reduces the number of wires that must be included in each of the cables 156, which in turn advantageously makes the cables more flexible and less cumbersome.

Figure 8:
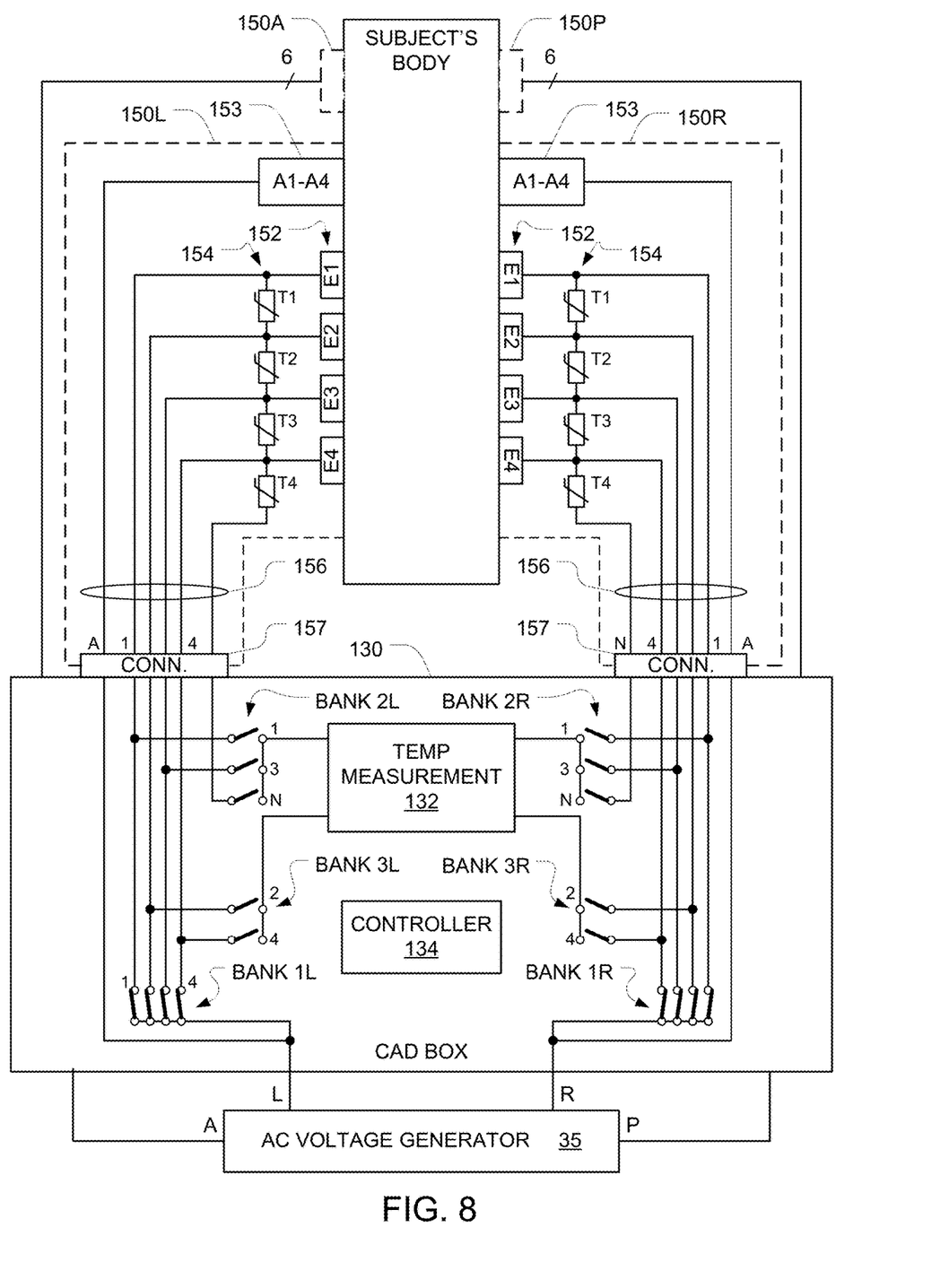
FIG. 8 is a block diagram of a system that uses four copies of the FIG. 7 transducer array to apply TTFields to a subject.

FIG. 8 is a block diagram of a system that uses four copies of the transducer array 150 (described above in connection with FIG. 7) to apply TTFields to a subject. In FIG. 8, these four copies are labeled 150A, 150P, 150L, and 150R, where A, P, L, and R stand for anterior, posterior, left, and right, respectively. The lower portion of FIG. 8 depicts an AC voltage generator 35 and a "CAD box" 130 as separate blocks, the latter of which includes a temperature measurement block 132, a controller 134, and banks of switches 1L, 2L, 3L, 1R, 2R, and 3R. In some embodiments, the components in those two blocks 35, 130 may be physically divided into two separate housings. But in alternative embodiments, the components in those two blocks 35, 130 are combined into a single housing.

For clarity, only the left and right channels are depicted in FIG. 8. But the remaining channels (i.e., the anterior and posterior channels) operate in the same way as the left and right channels, respectively. Additionally, each of the transducer arrays 150 in FIG. 8 is depicted with only 4 first electrode elements 152 and four thermistors 154 for purposes of clarity. But it is expected that practical systems will have a larger number (e.g., between 9 and 30) of first electrode elements and thermistors, and will also have a larger number of certain other components (e.g., switches, conductors, etc.), depending on the number of first electrode elements 152 that are actually used in each of the transducer arrays 150.

The FIG. 8 system can measure the temperatures of the thermistors 154 in the left channel 150L during the temperature-reading phase by controlling the electronically-controlled switches in banks 2L and 3L (which may be implemented using bidirectional analog switches) to select each of the thermistors in turn. For example, switches 1 and 2 should be closed to select thermistor T1; switches 2 and 3 should be closed to select thermistor T2; switches 3 and 4 should be closed to select thermistor T3; and switches 4 and N should be closed to select the last thermistor (i.e., T4 in FIG. 8). After any given one of the thermistors T1-T4 within the transducer array 150L has been selected, the temperature measurement block 132 can determine the temperature of that thermistor by measuring the resistance of the thermistor as described above in connection with FIG. 6.

Measuring the temperature of the thermistors 154 in the right channel 150R is accomplished using the same approach described above in connection with the left channel 150L, except that the banks of switches 2R and 3R are used instead of banks 2L and 3L. Corresponding banks of switches (not shown) are also provided for the other channels 150A, 150P, and a similar approach is used in those channels as well.

Assume that within a given interval of time (e.g., 1 second) during the current-outputting phase, the AC voltage generator 35 is applying an AC signal between the L and R terminals. This AC signal is applied to the A terminals of the left and right transducer arrays 150L, 150R, which means that the output of the AC voltage generator is applied to all of the second electrode elements 153 (A1-A4). Based on the temperature readings obtained from the thermistors 154 (T1-T4) during the temperature-reading phase, the controller 134 controls the switches in banks 1L and 1R (and the corresponding switches in the anterior and posterior channels, not shown) to either turn on or turn off the current (which originates in the AC voltage generator 35) to each of the corresponding first electrode elements 152 (E1-E4) during the next current-outputting phase as described above in connection with FIG. 6. For example, to leave the full current on for all four of the sets 152/153, all four of the switches in bank 1L should be closed. To reduce the current that passes through the E1/A1 set 152/153 of electrode elements (see FIG. 7), switch 1 in bank 1L should be opened; and to reduce the current that passes through the E2/A2 set 152/153 of electrode elements, switch 2 in bank 1L should be opened; etc.

As in the FIG. 5-6 embodiment, controlling the current that is routed through individual first electrode elements during the current-outputting phase can be used to reduce the current that passes through a given area when that area begins to get hot; and this can advantageously prevent overheating without completely turning off the current that passes through a given area.

In alternative embodiments, instead of implementing the temperature sensors using thermistors (as described above in connection with FIGS. 5-8), temperature sensing may be implemented using a plurality of regions of a pyroelectric material. Examples of suitable pyroelectric materials include PVDF homopolymers, PVDF organic derivatives e.g., P(VDF-TrFE), and PVDF-ceramic composites, where PVDF is poly(vinylidene fluoride) and TrFE is trifluoroethylene. In some embodiments, the pyroelectric material is Piezotech® RT-FC, which is a P(VDF-TrFE) copolymer. In some embodiments, the regions of pyroelectric material may be a polymer layer such as poly(vinylidene fluoride-trifluoroethylene-chlorotrifluoroethylene) and/or poly(vinylidene fluoride-trifluoroethylene-1-chlorofluoroethylene).

Each of the first and second electrode elements has a front face and a rear face. Each of the regions of the pyroelectric material has a front face and a rear face, and the front face of each of the regions of the pyroelectric material is disposed in electrical and thermal contact with the rear face of the respective set of first/second electrode elements. Additional electrode regions contact the rear face of the regions of the pyroelectric material.

The electrical and thermal contact between the front face of each of the regions of the pyroelectric material and the rear face of the respective set of first/second electrode elements may be achieved by placing those two faces in direct contact with each other (e.g., by depositing or spraying the first and second electrode elements onto the regions of the pyroelectric material during manufacturing). Alternatively, another layer of material that does not interrupt the electrical and thermal contact may be disposed between those two faces.

Because each of the first and second electrode elements is disposed in thermal contact with a respective one of the regions of the pyroelectric material, temperature variations of any given set of first/second electrode elements will cause a corresponding change in temperature in the respective region of the pyroelectric material. This change in temperature will cause a pyroelectric voltage to appear across opposite faces of the respective region of the pyroelectric material. The instantaneous value of this pyroelectric voltage can be measured via the first electrode elements and the additional electrode regions. And due to the thermal contact between the first and second electrode elements and the respective region of the pyroelectric material, the measured electrical signals not only represent the change in temperature of each region of the pyroelectric material—they also represent the change in temperature of each respective set of first/second electrode elements.

The regions of dielectric material may be discrete sections of a flexible polymer that are separated by gaps. Alternatively, the regions of dielectric material could be regions within a single contiguous sheet of a flexible polymer material.

Pyroelectric materials do not generate an output based on their absolute temperature. Instead, they generate an electrical output that is a function of a change in temperature. The first and second electrode elements are each positioned in thermal contact with a respective region of pyroelectric material with similar characteristics. So if a given set of electrode elements is running hotter than another set of electrode elements, the temperature fluctuations at the given set will be larger than the temperature fluctuations at the other set. And this will cause the region of pyroelectric material positioned in contact with the given set to generate a larger electrical output than the region of pyroelectric material positioned in contact with the other set.

A controller compares the temperature fluctuations of all the electrode sets by sampling the signals that are generated by the regions of pyroelectric material that are positioned in thermal contact with those electrode sets. By analyzing how the electrical characteristics change over time, the controller can determine whether the temperature fluctuations of a given set are larger than the temperature fluctuations of another set. The controller can then use this information to normalize the temperature of all the electrode elements by switching off the first electrode element within the hotter set to reduce the current that flows through the hotter set of electrode elements.

Because pyroelectric materials respond to changes in temperature (as opposed to absolute temperature), a pyroelectric material that is cycling between 37° C. and 37.2° C. will produce the same output as when that same pyroelectric material is cycling between 40° C. and a 40.2° C. In view of this, it is not sufficient to merely equalize the temperature of all the electrode elements within any given transducer array as described above. To the contrary—because the temperature of transducer arrays should be maintained below a given threshold (e.g., 40° C.), one more piece of information is needed to ensure that the transducer arrays do not overheat. And this additional piece of information is the absolute temperature of at least one set of first/second electrode elements. For if the absolute temperature of a single set of first/second electrode elements is known, and it is also known that the temperatures of all of the electrode elements have been equalized, we can then be sure that none of the electrode elements are hotter than the threshold temperature.

In view of this, at least one absolute temperature sensor (e.g., a thermistor) is positioned in thermal contact with at least one set of first/second electrode elements, and the system includes a circuit so that the controller can determine the temperature of the thermistor (and thereby determine the temperature of the electrode element that is in thermal contact with the thermistor).

Figure 9:
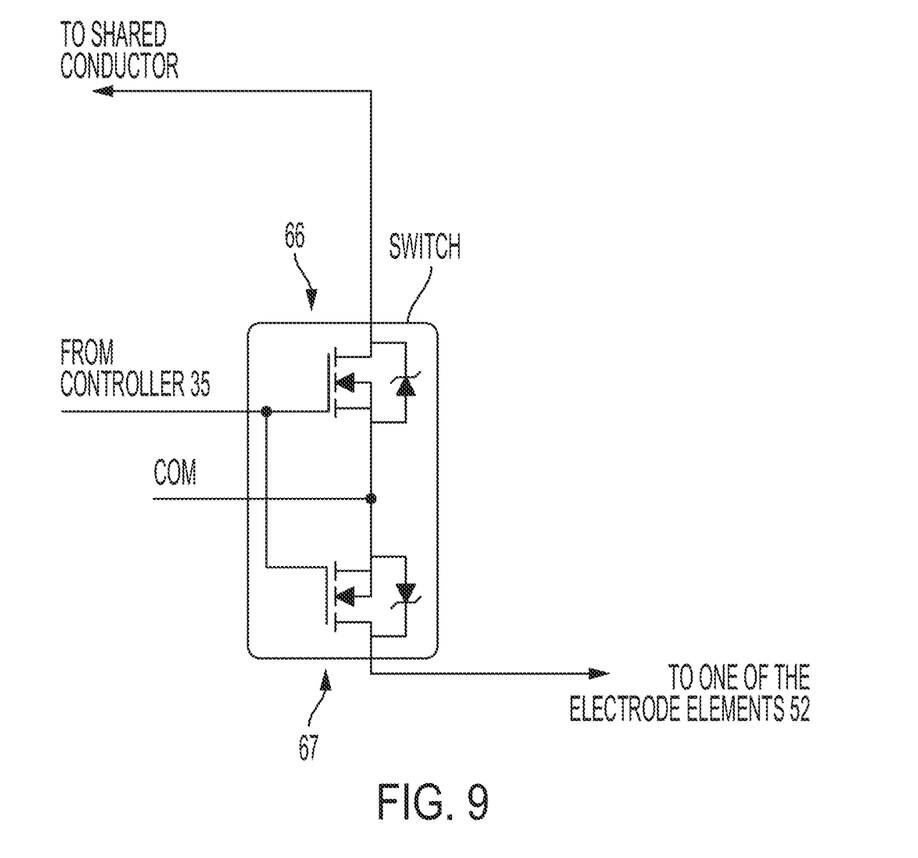
FIG. 9 is a schematic diagram of a circuit that is suitable for implementing each of the switches in banks 1L and 1R in the FIG. 6 and FIG. 8 embodiments.

FIG. 9 is a schematic diagram of a circuit that is suitable for implementing each of the switches in banks 1L and 1R in the FIG. 6 and FIG. 8 embodiments described above, as well as the corresponding banks for the anterior and posterior channels (not shown). The circuit includes two field effect transistors (FET) 66, 67 wired in series, which is a configuration that can pass current in either direction. One example of a suitable FET for this circuit is the BSC320N20NSE (Infineon Technologies AG, Neubiberg, Germany). (Note that the diodes depicted in FIG. 9 are inherently included within the FETs 66, 67 themselves.) The series combination of the two FETs 66, 67 will either conduct or block the flow of electricity, depending on the state of the control input that arrives from one of the digital outputs of the controller 34 described above. When the series combination is conducting, current can flow between the shared conductor and the respective first electrode element 52. On the other hand, when the series combination of FETs 66, 67 is not conducting, current will not flow between the shared conductor and the respective first electrode element 52.

In the embodiments described above in connection with FIGS. 5 and 7, all of the electrode elements 52, 53 are capacitively coupled, and the support structure 59 is configured to hold the electrode elements 52, 53 against the subject's body so that the dielectric layer of the electrode elements 52, 53 faces the subject's body and can be positioned in contact with the subject's body. But in alternative embodiments, electrode elements that are not capacitively coupled may be used. In this case, the dielectric layer of each electrode element is omitted, in which case the support structure 59 holds the electrode elements 52, 53 against the subject's body so a conductive surface of the electrode elements 52, 53 faces the subject's body and can be positioned in contact with the subject's body. Optionally, in these embodiments, a layer of hydrogel may be disposed between the conductive surface of the electrode elements 52, 53 and the subject's body when the transducer array 50 is placed against the subject's body.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for applying an alternating electric field to a subject's body, the apparatus comprising:
    at least four sets of electrode elements, wherein each of the sets of electrode elements includes a respective first electrode element and a respective second electrode element disposed in thermal contact with the respective first electrode element;
    a connector having at least four first pins and a second pin;
    at least four first conductors, each of which provides an electrically conductive path between (a) a respective one of the first pins and (b) a respective one of the first electrode elements;

a second conductor that provides an electrically conductive path between the second pin and all of the second electrode elements;

at least four temperature sensors, each of which is disposed in thermal contact with a respective one of the sets of electrode elements; and a support configured to hold the sets of electrode elements against the subject's body.

2. The apparatus of claim 1, wherein within each of the sets of electrode elements, the area of the respective second electrode element is at least double the area of the respective first electrode element.

3. The apparatus of claim 1, wherein the apparatus has at least nine sets of electrode elements, wherein the connector has at least nine first pins, wherein the apparatus has at least nine first conductors, and wherein the apparatus has at least nine temperature sensors.

4. The apparatus of claim 1, wherein each of the temperature sensors comprises a thermistor having a first terminal and a second terminal, wherein the connector has a third pin, wherein each of the first conductors provides an electrically conductive path between (a) a respective one of the first pins, (b) a respective one of the first electrode elements, and (c) the first terminal of a respective thermistor, and wherein the apparatus further comprises a third conductor that provides an electrically conductive path between the third pin and the second terminal of at least one of the thermistors.

5. The apparatus of claim 4, wherein the second terminals of all the thermistors are wired together.

6. The apparatus of claim 4, wherein the thermistors are wired in series, beginning with a first one of the thermistors and ending with a last one of the thermistors, and wherein the second terminal of each of the thermistors except for the last thermistor is wired to the first terminal of a respective subsequent thermistor, and wherein the third conductor provides an electrically conductive path between the third pin of the connector and the second terminal of the last thermistor.

7. The apparatus of claim 1, wherein each of the temperature sensors comprises a region of a pyroelectric material.

8. The apparatus of claim 1, wherein each of the first electrode elements comprises a conductive plate with a dielectric layer disposed thereon, wherein each of the second electrode elements comprises a conductive plate with a dielectric layer disposed thereon, and wherein the support is configured to hold the first electrode elements and the second electrode elements against the subject's body so that the dielectric layers of the first electrode elements and the dielectric layers of the second electrode elements face the subject's body.

* * * * *